(12) United States Patent
Ware et al.

(10) Patent No.: US 10,744,309 B1
(45) Date of Patent: Aug. 18, 2020

(54) MEDICINAL APPLICATOR

(71) Applicants: Stephen Ware, Norfolk, VA (US); Charlotte Ware, Norfolk, VA (US)

(72) Inventors: Stephen Ware, Norfolk, VA (US); Charlotte Ware, Norfolk, VA (US)

( * ) Notice: Subject to any disclaimer, the term of this patent is extended or adjusted under 35 U.S.C. 154(b) by 398 days.

(21) Appl. No.: 15/677,117

(22) Filed: Aug. 15, 2017

(51) Int. Cl.
*A61M 35/00* (2006.01)
*A61F 13/40* (2006.01)

(52) U.S. Cl.
CPC ......... *A61M 35/003* (2013.01); *A61M 35/006* (2013.01); *A61M 2205/0216* (2013.01); *A61M 2205/3337* (2013.01); *A61M 2209/084* (2013.01)

(58) Field of Classification Search
CPC .......... A61M 35/003; A61M 2209/084; A61M 2205/0216; A61M 2205/3337; A61M 35/006; A47L 1/08; A47L 13/22
USPC ... 401/138, 139, 239, 222, 131, 6, 140, 183, 401/186, 205, 207
See application file for complete search history.

(56) References Cited

U.S. PATENT DOCUMENTS

| | | | | |
|---|---|---|---|---|
| 4,171,171 A * | 10/1979 | Jones | ...................... | A45D 34/04 401/150 |
| 4,925,327 A * | 5/1990 | Wirt | ..................... | A61M 35/006 401/132 |
| 5,322,382 A * | 6/1994 | Hull | ....................... | A45D 34/04 401/131 |
| 6,210,057 B1 * | 4/2001 | Yannaci | ............... | A45D 34/042 401/150 |
| D497,450 S | 10/2004 | Scofield | | |
| 6,964,536 B1 | 11/2005 | Alhateeb | | |
| 2003/0170066 A1 | 9/2003 | White | | |
| 2006/0208142 A1 * | 9/2006 | Adams, IV | ............. | F16B 45/00 248/206.2 |
| 2007/0157408 A1 | 7/2007 | Bargiel | | |
| 2009/0003917 A1 | 1/2009 | Duncan | | |
| 2010/0168638 A1 * | 7/2010 | Korogi | ................ | A61M 35/006 604/3 |
| 2010/0286637 A1 * | 11/2010 | Cable, Jr. | ............ | A61M 35/003 604/310 |
| 2012/0097183 A1 | 4/2012 | Miller | | |
| 2012/0282006 A1 | 11/2012 | Heil | | |
| 2013/0341430 A1 * | 12/2013 | Hall | ....................... | F23R 3/283 239/533.2 |
| 2015/0352344 A1 | 12/2015 | Cotton | | |

FOREIGN PATENT DOCUMENTS

EP 2196105 A 6/2010

* cited by examiner

*Primary Examiner* — Ophelia A Hawthorne
*Assistant Examiner* — Heather K Barnwell

(57) ABSTRACT

The medicinal applicator is a device that applies a therapeutic liquid to a patient. The medicinal applicator extends the reach of the patient such that the patient can apply the therapeutic liquid to the back of the patient. The medicinal applicator includes a handle, a dispensing assembly, one or more applicators, a wicking structure and a wall mount. The dispensing assembly is mounted in the handle. The dispensing assembly transports the therapeutic liquid to an applicator selected from the one or more applicators. The selected applicator attaches to the handle. The selected applicator transports the therapeutic liquid from the dispensing assembly to the wicking structure. From the wicking structure the therapeutic liquid is applied to the patient. The wall mount allows the medicinal applicator to be hung from a wall.

1 Claim, 6 Drawing Sheets

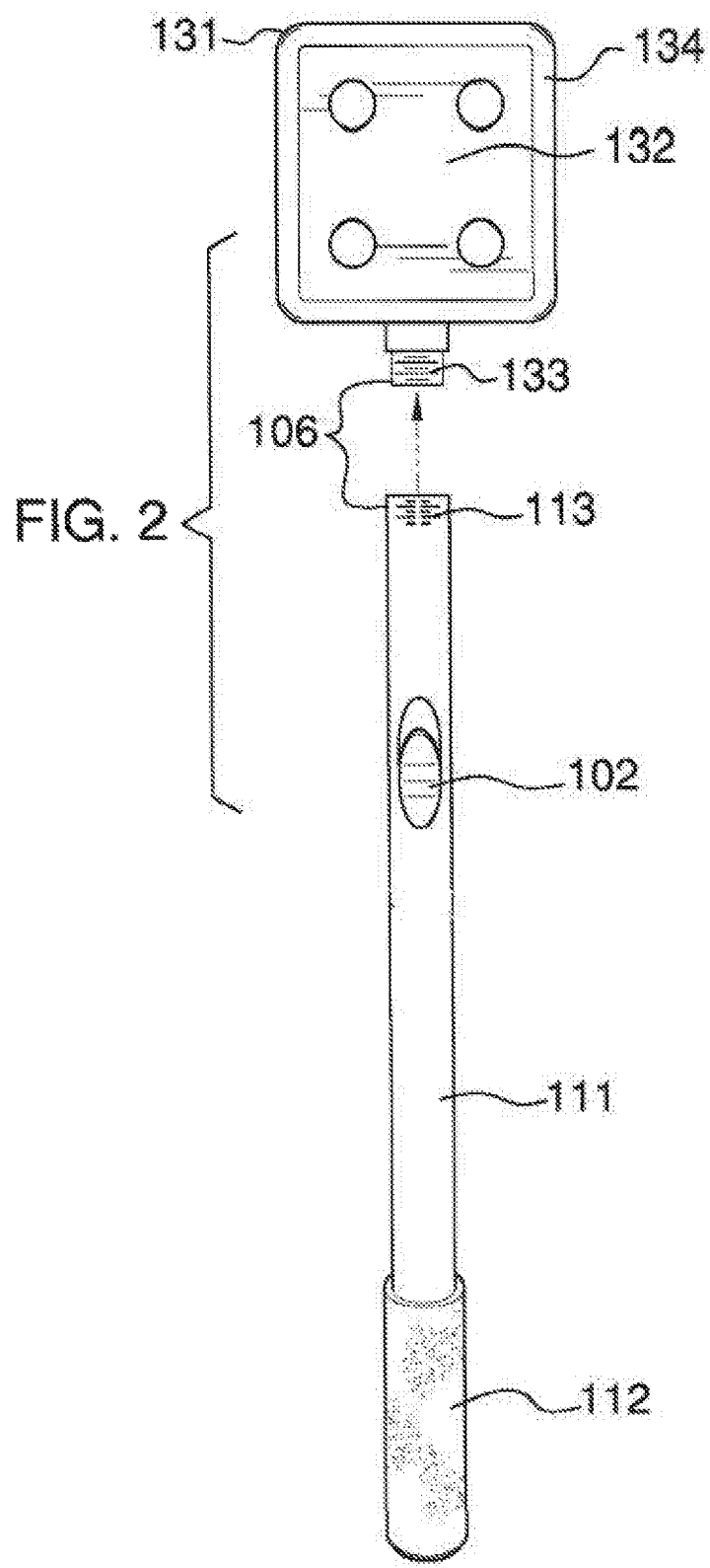

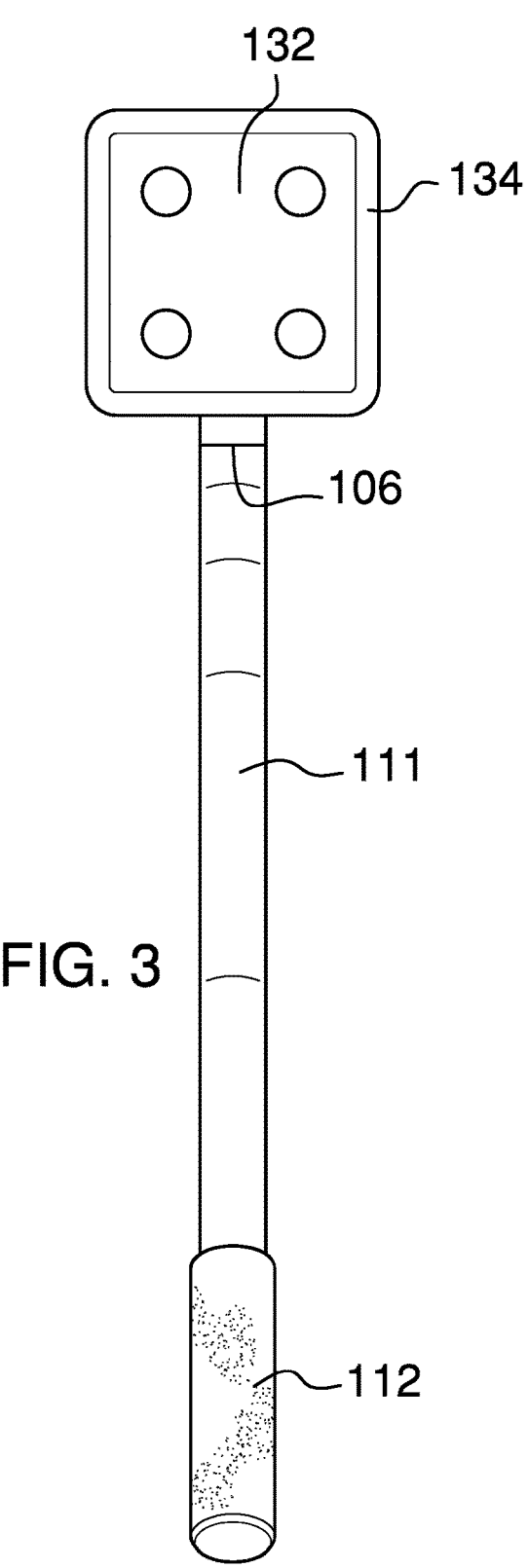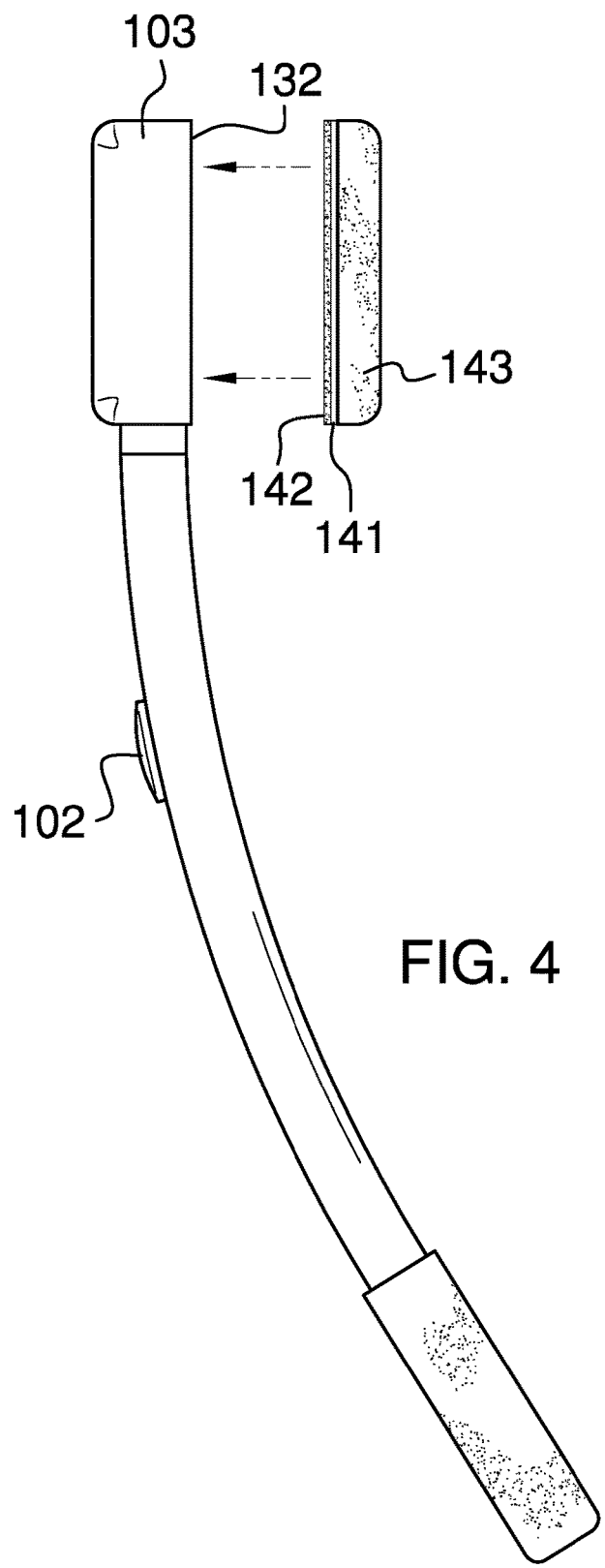

MEDICINAL APPLICATOR

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including a device for introducing media on to a body, more specifically, a handheld instrument for applying an spreading a media on to the body.

SUMMARY OF INVENTION

The medicinal applicator is configured for use with a therapeutic liquid. The medicinal applicator is adapted for use with a patient. The medicinal applicator is a device that applies the therapeutic liquid to the patient. The medicinal applicator extends the reach of the patient such that the patient can apply the therapeutic liquid to the back of the patient. The medicinal applicator comprises a handle, a dispensing assembly, one or more applicators, a wicking structure and a wall mount. The dispensing assembly is mounted in the handle. The dispensing assembly transports the therapeutic liquid to an applicator selected from the one or more applicators. The selected applicator attaches to the handle. The selected applicator transports the therapeutic liquid from the dispensing assembly to the wicking structure. From the wicking structure the therapeutic liquid is applied to the patient. The wall mount allows the medicinal applicator to be hung from a wall.

These together with additional objects, features and advantages of the medicinal applicator will be readily apparent to those of ordinary skill in the art upon reading the following detailed description of the presently preferred, but nonetheless illustrative, embodiments when taken in conjunction with the accompanying drawings.

In this respect, before explaining the current embodiments of the medicinal applicator in detail, it is to be understood that the medicinal applicator is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the medicinal applicator.

It is therefore important that the claims be regarded as including such equivalent construction insofar as they do not depart from the spirit and scope of the medicinal applicator. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 2 is an exploded view of an embodiment of the disclosure.

FIG. 3 is a front view of an embodiment of the disclosure.

FIG. 4 is a side view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
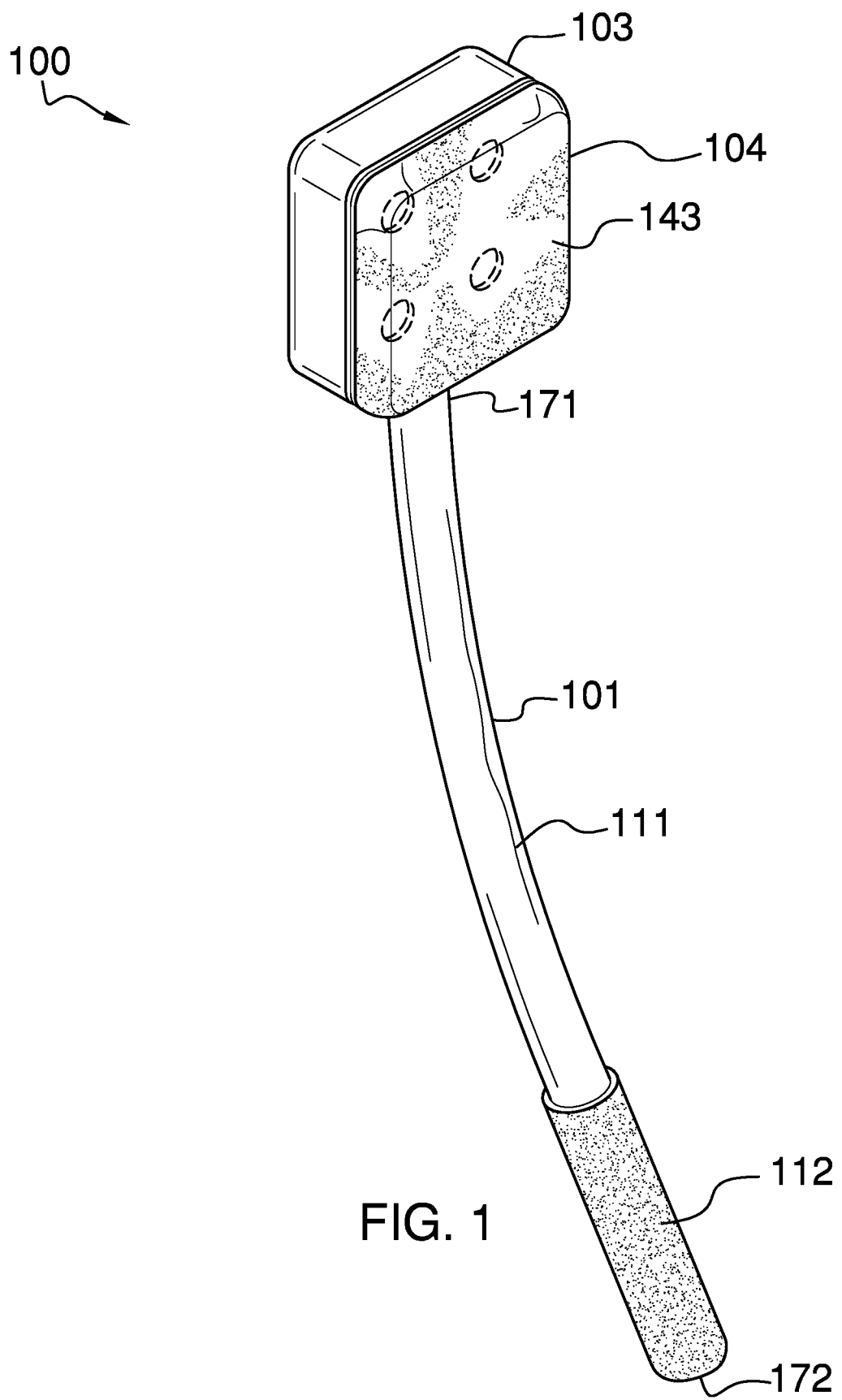
FIG. 1 is a perspective view of an embodiment of the disclosure.
Figure 5:
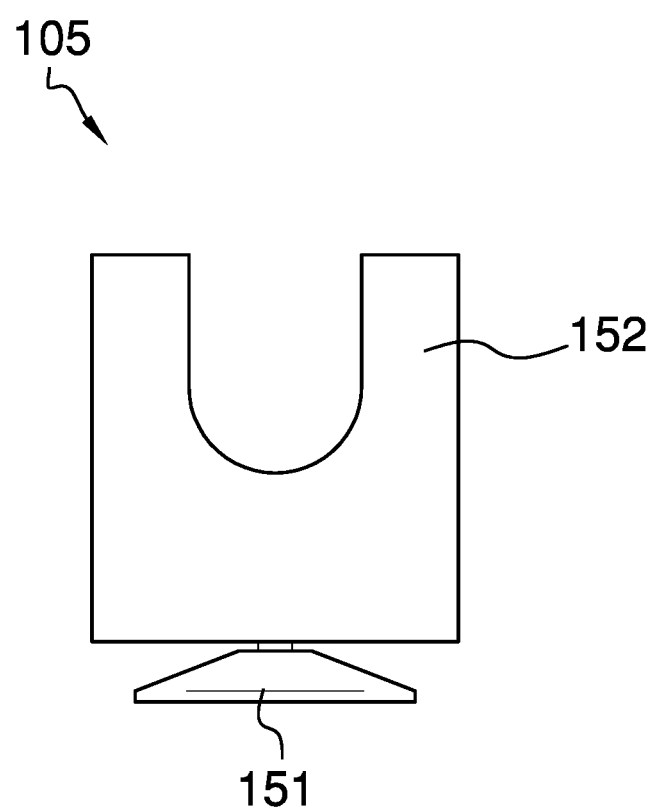
FIG. 5 is a detail view of an embodiment of the disclosure.
Figure 6:
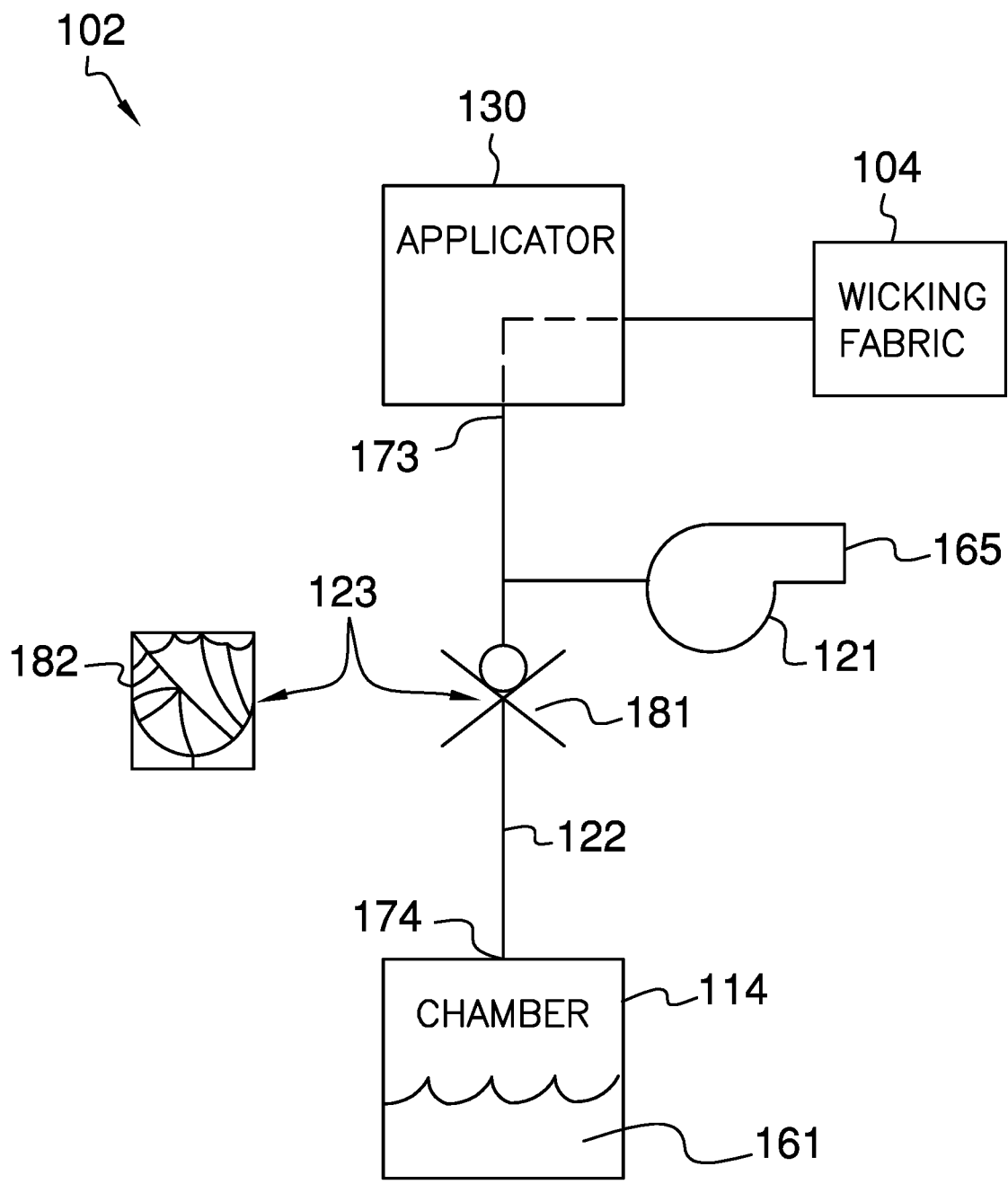
FIG. 6 is a block diagram or schematic view of an embodiment of the disclosure.
Figure 7:
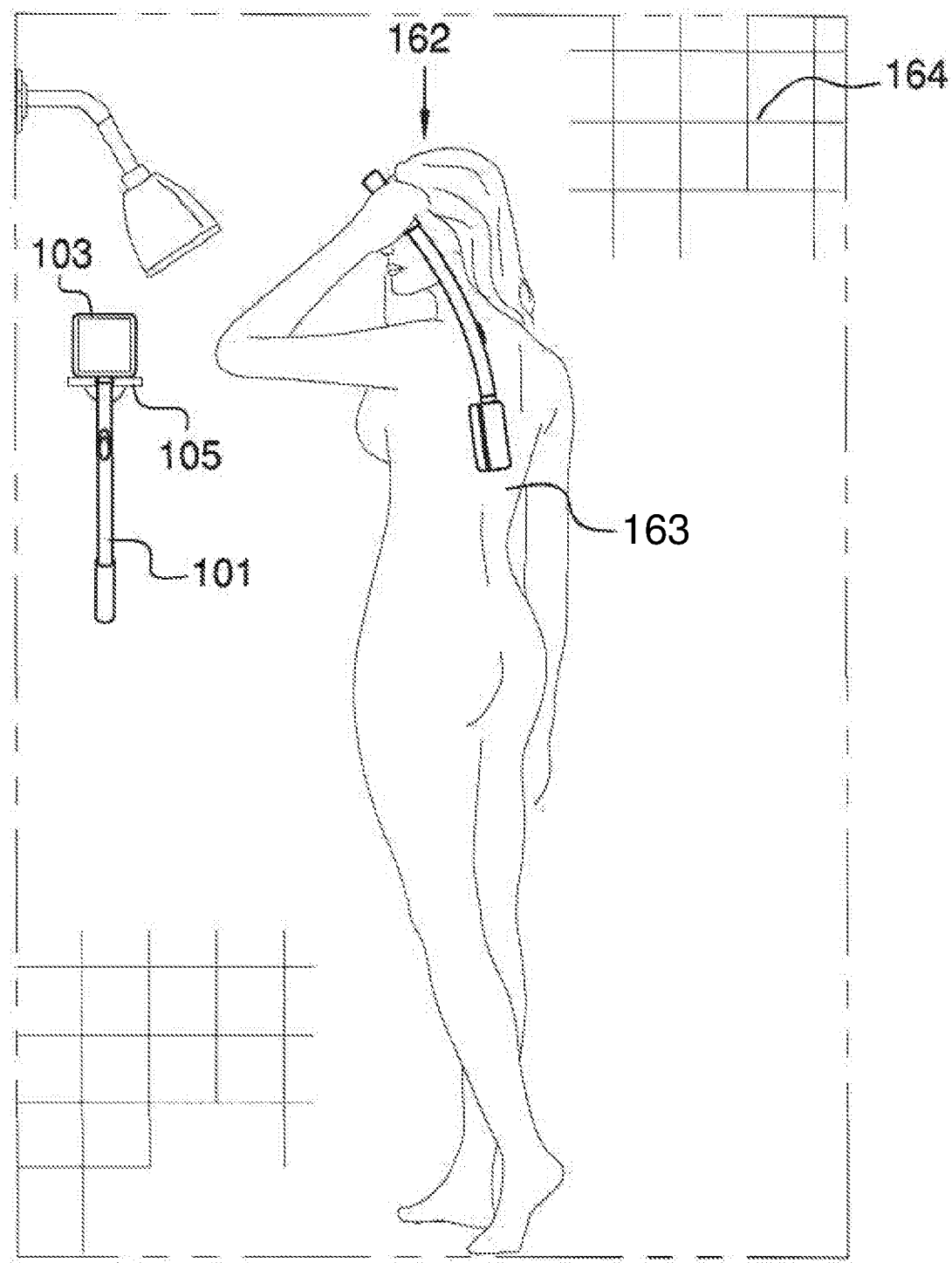
FIG. 7 is an in-use view of an embodiment of the disclosure.

Detailed reference will now be made to one or more potential embodiments of the disclosure, which are illustrated in FIGS. 1 through 7.

The medicinal applicator 100 (hereinafter invention) is configured for use with a therapeutic liquid 161. The therapeutic liquid 161 refers to a liquid that is intended to be applied to the patient 162. The invention 100 is adapted for use with a patient 162. The patient 162 refers to an individual designated to receive the therapeutic liquid 161. The patient 162 is further defined with a back 163. The invention 100 is a device that applies the therapeutic liquid 161 to the patient 162. The invention 100 extends the reach of the patient 162 such that the patient 162 can apply the therapeutic liquid 161 to the back 163 of the patient 162. The invention 100 comprises a handle 101, a dispensing assembly 102, one or more applicators 103, a wicking structure 104 and a wall 164 mount 105. The dispensing assembly 102 is mounted in the handle 101. The dispensing assembly 102 transports the therapeutic liquid 161 to an applicator 130 (hereinafter individual applicator) selected from the one or more applicators 103. The individual applicator 130 attaches to the handle 101. The individual applicator 130 transports the therapeutic liquid 161 from the dispensing assembly 102 to the wicking structure 104. From the wicking structure 104 the therapeutic liquid 161 is applied to the patient 162. The wall 164 mount 105 allows the invention 100 to be hung from a wall 164. The wall 164 refers to a vertical surface upon which the invention 100 will be hung.

The invention 100 further comprises a threaded connection 106. The threaded connection 106 is a fastening device that removably attaches an individual applicator 130 to the handle 101. The threaded connection 106 is formed using the interior screw thread 113 and the exterior screw thread 133. The threaded connection 106 is formed by attaching the exterior screw thread 133 to the interior screw thread 113. The exterior screw thread 133 to the interior screw thread 113 are discussed in greater detail elsewhere in this disclosure. Threaded connections are discussed in greater detail elsewhere in this disclosure.

The handle 101 is a rigid structure formed in the manner of a center capped tube. The center capped tubular structure of the handle 101 forms a reservoir 114 that stores the therapeutic liquid 161 before use. The handle 101 comprises a tube 111, a grip 112, an interior screw thread 113, and a reservoir 114. The handle 101 is further defined with a first end 171 and a second end 172.

The tube 111 is a rigid center capped tubular structure. In the first potential embodiment of the disclosure, as shown most clearly in FIGS. 1 and 4, the tube 111 is formed with an arcuate curvature that makes the therapeutic liquid 161 easier for a patient 162 to apply.

The grip 112 is an elastomeric material that is applied to the second end 172 of the tube 111.

The interior screw thread 113 is the element of the threaded connection 106 that is associated with the handle 101. The interior screw thread 113 is formed on the interior surface of the tube 111 at the first end 171 of the tube 111. Interior screw threads 113 and threaded connections 106 are discussed in greater detail elsewhere in this disclosure.

The reservoir 114 refers to a chamber formed between the center barrier of the tube 111 and the first end 171 of the tube 111. The reservoir 114 is a fluid impermeable structure. A stock of the therapeutic liquid 161 is stored within the reservoir 114. The therapeutic liquid 161 is introduced into the reservoir 114 through the first end 171 of the tube 111.

The dispensing assembly 102 is a fluid transport mechanism that delivers the therapeutic liquid 161 stored within the handle 101 to an individual applicator 130 selected from the one or more applicators 103 and its associated wicking structure 104. The dispensing assembly 102 comprises a pump 121, a draw tube 122, and a check valve 123. The draw tube 122 is further defined with a third end 173 and a fourth end 174.

The pump 121 is a mechanical device that creates a vacuum within the draw tube 122 by expelling air contained within the draw tube 122 into the atmosphere 165. The vacuum created by the pump 121 draws the therapeutic liquid 161 into the draw tube 122 towards the individual applicator 130.

The fourth end 174 of the draw tube 122 is inserted into the therapeutic liquid 161 contained within the reservoir 114. The third end 173 of the draw tube 122 attaches to the manifold 131 of the individual applicator 130. The manifold 131 is discussed in greater detail elsewhere in this disclosure.

The check valve 123 is a type of valve that allows fluids to flow in only a single direction. The check valve 123 is selected from the group consisting of a tesla valve 182 and a ball valve 181. In the first potential embodiment of the disclosure, as shown most clearly in FIG. 6, the check valve 123 is configured to allow air to be expelled from the draw tube 122 into the atmosphere 165 by the pump 121. The check valve 123 is discussed in greater detail elsewhere in this disclosure.

Each of the one or more applicators 103 is a manifold 131 that is removably attached to the handle 101. Each of the one or more applicators 103: 1) receives the therapeutic liquid 161 from the handle 101 through the dispensing assembly 102; and, 2) dispenses the therapeutic liquid 161 to the wicking structure 104. The one or more applicators 103 comprises a collection of one or more individual applicators 130. The individual applicator 130 attaches to the first end 171 of the tube 111 using the threaded connection 106. The selection of the individual applicator 130 from the one or more applicators 103 is determined by the viscosity of the therapeutic liquid 161.

Each individual applicator 130 comprises a manifold 131, a foraminous surface 132, an exterior screw thread 133, and a margin perimeter 134.

The manifold 131: 1) receives the therapeutic liquid 161 under pressure; and, 2) distributes the therapeutic liquid 161 to the foraminous surface 132 wherein the therapeutic liquid 161 is dispensed through the wicking structure 104. The manifold 131 is formed in the shape of a rectilinear block.

The foraminous surface 132 is formed on the face of the manifold 131 with the largest surface area. The foraminous surface 132 is formed with a plurality of apertures through which the therapeutic liquid 161 is released from the individual applicator 130. The margin perimeter 134 is a border formed along the perimeter of the foraminous surface 132. The margin perimeter 134 is a smooth rectilinear surface that: 1) does not contain any of the apertures that define the foraminous surface 132; and, 2) that is coaxially positioned around the foraminous portion of the foraminous surface 132.

The exterior screw thread 133 is the element of the individual applicator 130 that is associated with the threaded connection 106. The exterior screw thread 133 is hollow tubular projection that is formed on a face of the manifold 131. The exterior screw thread 133 is sized such that the exterior screw thread 133 can be attached to the interior screw thread 113 to form the threaded connection 106. The exterior screw thread 133 attaches to the dispensing assembly 102 such that the therapeutic liquid 161 will pass through the threaded connection 106 into the manifold 131. Exterior screw threads 133 and threaded connections 106 are discussed in greater detail elsewhere in this disclosure.

The wicking structure 104 is a structure that uses capillary action to draw the therapeutic liquid 161 out of the associated individual applicator 130 such that the therapeutic liquid 161 can be applied to the patient 162. The wicking structure 104 comprises a frame 141, an adhesive 142 and a wicking fabric 143. The wicking structure 104 attaches to the margin perimeter 134 of the individual applicator 130.

The frame 141 rectilinear boundary structure: 1) to which the wicking fabric 143 is attached; and, 2) which attaches the wicking structure 104 to the dispensing assembly 102. The shape of the frame 141 is congruent with the shape of the margin perimeter 134 such that the frame 141 may be aligned with and overlaid on the margin perimeter 134. The frame 141 attaches to the margin perimeter 134 of the foraminous surface 132 using the adhesive 142.

The adhesive 142 is a commercially available removable adhesive that is applied to the frame 141 of the wicking structure 104. The adhesive 142 is a removable and repositionable adhesive that: 1) allows the wicking structure 104 to be replaced; and, 2) allows the wicking structure 104 to be reused.

The wicking fabric 143 is a textile that is formed from hydrophobic filaments. The wicking fabric 143 is constructed such that the capillary action between the filaments of the wicking fabric 143 will transport the therapeutic liquid 161 through the wicking fabric 143 in a manner that makes the therapeutic liquid 161 available for application. The wicking fabric 143 attaches to the frame 141. The frame 141 is formed with a hollow interior such that the wicking fabric 143 is placed in contact with the foraminous surface 132 during use of the invention 100.

The wall 164 mount 105 is a support that attaches to a wall 164 such that the invention 100 may be hung from the wall 164 mount 105. The wall 164 mount 105 comprises a suction cup 151 and a U hook 152. The suction cup 151 is a well-known and commercially available device that attaches the U hook 152 to a wall 164. The suction cup 151 is discussed in greater detail elsewhere in this disclosure. The U hook 152 is a readily and commercially available structure from which the invention 100 may be hung. The U hook 152 is often called a tool hook.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Arcuate: As used in this disclosure, arcuate describes the curve formed by a bent bow.

Ball Valve: As used in this disclosure, a ball valve is a type of commercially available check valve.

Capillary Action: As used in this disclosure, capillary action refers to the tendency of a liquid to experience adhesion forces when exposed to surface or surfaces formed within a narrow structure and the tendency of a liquid to flow as a result of these adhesion force. In the proper circumstances, the adhesive forces of capillary action can overcome gravitational forces or the intermolecular forces that form liquids. The span of the lengths where capillary action predominates is often referred to as a microfluidic scale. On a practical level, the concept of wicking and wicking fabrics rely primarily on capillary action.

Capped Tube: As used in this disclosure, a capped tube is a tube with one closed end and one open end.

Center Capped Tube: As used in this disclosure, a center capped tube is a tube with a first open end, a second open end, and a barrier that is fabricated within the tube. The barrier prevents the flow of liquid or gas from the first open end of the tube through to the second open end of the tube.

Check Valve: As used in this disclosure, a check valve is a valve that permits the flow of fluid or gas in a single direction. Within selected potential embodiments of this disclosure, the check valve is a commercially available product that is selected from the group consisting of a ball valve and a Tesla valve.

Coaxial: As used in this disclosure, coaxial is an term that refers to a first object that is inserted or contained within a second object such: 1) that the first object and the second object share the same center point if the or first object and the second object are treated as a two dimensional objects; or, 2) that the first object and the second object share the same center axis if the or first object and the second object are treated as a prism.

Congruent: As used in this disclosure, congruent is a term that compares a first object to a second object. Specifically, two objects are said to be congruent when the perimeter, diameter, or shape of the first object can be superimposed over the perimeter, diameter, or shape of the second object such that the perimeter, diameter, or shape of the first object coincides, within manufacturing tolerances, with the perimeter, diameter, or shape of the second object Elastic: As used in this disclosure, an elastic is a material or object that deforms when a force is applied to it and that is able to return to its relaxed shape after the force is removed. A material that exhibits these qualities is also referred to as an elastomeric material.

Exterior: As used in this disclosure, the exterior is use as a relational term that implies that an object is not contained within the boundary of a structure or a space.

Exterior Screw Thread: An exterior screw thread is a ridge wrapped around the outer surface of a tube in the form of a helical structure that is used to convert rotational movement into linear movement.

Fiber: As used in this disclosure, a fiber is a slender elongated structure.

Filament: As used in this disclosure, a filament is a thread like fiber or object that is used in the production of a yarn.

Fluid: As used in this disclosure, a fluid refers to a state of matter wherein the matter is capable of flow and takes the shape of a container it is placed within. The term fluid commonly refers to a liquid or a gas.

Foraminous: As used in this disclosure, foraminous is an adjective that describes a surface, plate, or platform that is perforated with a plurality of holes.

Grip: As used in this disclosure, a grip is an accommodation formed within an object that allows the object to be grasped or manipulated by a hand.

Handle: As used in this disclosure, a handle is an object by which a tool, object, or door is held or manipulated with the hand.

Hang: As used in this disclosure, to hang an object is to suspend an object above a surface from above such that the inferior end of the object can move freely.

Hydrophobic: As used in this disclosure, hydrophobic refers to a substance that repels and does not mix with water. Hydrophobic materials are often selected because they will not absorb water.

Interior: As used in this disclosure, the interior is use as a relational term that implies that an object is contained within the boundary of a structure or a space.

Interior Screw Thread: An interior screw thread is a groove that is formed around the inner surface of a tube in the form of a helical structure that is used to convert rotational movement into linear movement.

Liquid: As used in this disclosure, a liquid refers to a state of matter that is fluid and that maintains, for a given pressure, a fixed volume that is independent of the volume of the container.

Manifold: As used in this disclosure, a manifold is a pipe or chamber having several ports through which liquid or gas is gathered or distributed.

Patient: As used in this disclosure, a patient is a person who is designated to receive a medical treatment, therapy or service. The term patient may be extended to an animal when used within the context of the animal receiving veterinary treatment or services Pump: As used in this disclosure, a pump is a mechanical device that uses suction or pressure to raise or move fluids, compress fluids, or force a fluid into an inflatable object.

Rectangular Block: As used in this disclosure, a rectangular block refers to a three dimensional structure comprising six rectangular surfaces formed at right angles. Within this disclosure, a rectangular block may further comprise rounded edges and corners.

Rectilinear: As used in this disclosure, rectilinear is an adjective that is used to describe an object that: 1) moves in a straight line or lines; 2) consists of a straight line or lines; 3) is bounded by a straight line or lines; or, 4) is otherwise characterized by a straight line or lines.

Rectilinear Block: As used in this disclosure, a rectilinear block refers to a three dimensional structure comprising a plurality of rectangular surfaces. Rectilinear blocks are similar to rectangular blocks and are often used to create a structure with a reduced interior volume relative to a rectangular block. Within this disclosure, a rectilinear block may further comprise rounded edges and corners.

Removable Adhesive: As used in this disclosure, a removable adhesive is a commercially available adhesive that is designed with a lower tack, or stickiness, such that a first object is attached to a second object with a removable adhesive the first object can be readily removed in a manner that ideally, though not necessarily practically, leaves behind no adhesive residue on the second object. A repositionable adhesive is a subset of removable adhesives that are intended to allow the first object to be reattached to a third object or the second object in the initial or a different position. Within this disclosure, a removable adhesive is assumed to include repositionable adhesives.

Rounded: A used in this disclosure, the term rounded refers to the replacement of an apex, vertex, or edge of a structure with a (generally smooth) curvature wherein the concave portion of the curvature faces the interior or center of the structure.

Suction Cup: As used in this disclosure, a suction cup means an object or device that uses negative fluid pressure of air or water to adhere to nonporous surfaces by creating a partial vacuum.

Tack: As used in this disclosure, tack refers to a measure of the bonding strength of an adhesive. The greater the bonding strength the more tack the adhesive is said to have.

Tesla Valve: As used in this disclosure, a Tesla valve is a type of check valve that requires the use of no moving parts.

Textile: As used in this disclosure, a textile is a material that is woven, knitted, braided or felted. Synonyms in common usage for this definition include fabric and cloth.

Therapeutic: As used in this disclosure, therapeutic is an adjective that refers to a medical, ameliorative, or hygienic substance, process, or procedure.

Threaded Connection: As used in this disclosure, a threaded connection is a type of fastener that is used to join a first tube shaped and a second tube shaped object together. The first tube shaped object is fitted with fitted with a first fitting selected from an interior screw thread or an exterior screw thread. The second tube shaped object is fitted with the remaining screw thread. The tube shaped object fitted with the exterior screw thread is placed into the remaining tube shaped object such that: 1) the interior screw thread and the exterior screw thread interconnect; and, 2) when the tube shaped object fitted with the exterior screw thread is rotated the rotational motion is converted into linear motion that moves the tube shaped object fitted with the exterior screw thread either into or out of the remaining tube shaped object. The direction of linear motion is determined by the direction of rotation.

Tube: As used in this disclosure, a tube is a hollow cylindrical device that is used for transporting liquids and gases. The line that connects the center of the first base of the cylinder to the center of the second base of the cylinder is referred to as the center axis of the tube or the centerline of the tube. In this disclosure, the terms inner diameter of a tube and outer diameter of a tube are used as they would be used by those skilled in the plumbing arts.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

Viscosity: As used in this disclosure, viscosity refers to the resistance of a liquid or an elastic material to deformation. Higher viscosity would refer to a greater resistance to flow or to deformation.

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A medical device comprising:
    a handle, a dispensing assembly, one or more applicators, a wicking structure, and a threaded connection;
    wherein the medical device is configured for use with a therapeutic liquid;
    wherein the therapeutic liquid is stored in the handle;
    wherein the medical device is adapted for use with a patient;
    wherein the medical device is adapted to apply the therapeutic liquid to the patient;
    wherein the dispensing assembly is mounted in the handle;
    wherein the dispensing assembly transports the therapeutic liquid to an individual applicator selected from the one or more applicators;
    wherein the threaded connection is a fastening device that removably attaches individual applicator;
    wherein the individual applicator transports the therapeutic liquid from the dispensing assembly to the wicking structure;
    wherein the wicking structure is adapted to apply the therapeutic liquid to the patient;
    wherein the handle is a rigid structure;
    wherein the handle comprises a tube, an interior screw thread, and a reservoir;
    wherein the handle is further defined with a first end and a second end;
    wherein the reservoir and the interior screw thread are formed within the handle;

wherein the tube is a center capped tube;
wherein the tube is formed with an arcuate curvature;
wherein the interior screw thread is formed on an interior surface of the tube at the first end of the tube;
wherein the reservoir is a chamber formed between a center barrier of the tube and the first end of the tube;
wherein the reservoir is a fluid impermeable structure;
wherein the therapeutic liquid is stored within the reservoir;
wherein the therapeutic liquid is introduced into the reservoir through the first end of the handle;
wherein the dispensing assembly is a fluid transport mechanism;
wherein the dispensing assembly transports the therapeutic liquid stored within the reservoir to an individual applicator;
wherein the dispensing assembly comprises a pump, a draw tube, and a check valve;
wherein the draw tube is further defined with a third end and a fourth end;
wherein the pump, the draw tube, and the check valve are fluidically interconnected;
wherein the fourth end of the draw tube is inserted into the therapeutic liquid contained within the reservoir;
wherein the third end of the draw tube attaches to the individual applicator;
wherein the pump is a mechanical device;
wherein the pump creates a vacuum within the draw tube;
wherein the vacuum created by the pump draws the therapeutic liquid into the draw tube towards the individual applicator;
wherein the check valve allows the therapeutic liquid to flow in a single direction;
wherein each individual applicator selected from the one or more applicators receives the therapeutic liquid from the handle through the dispensing assembly;
wherein each individual applicator dispenses the therapeutic liquid to the wicking structure;
wherein each individual applicator comprises a manifold, a foraminous surface, an exterior screw thread, and a margin perimeter;
wherein the exterior screw thread, the foraminous surface, and the margin perimeter attach to the manifold;
wherein the exterior screw thread attaches to the interior screw thread of the tube to form the threaded connection;
wherein the therapeutic fluid flows through the threaded connection;
wherein the manifold receives the therapeutic liquid under pressure;
wherein the manifold distributes the therapeutic liquid to the foraminous surface;
wherein the manifold is formed in the shape of a rectilinear block;
wherein the foraminous surface is formed on the manifold with a largest surface area;
wherein the foraminous surface is formed with a plurality of apertures through which the therapeutic liquid flows;
wherein the margin perimeter is a border formed along a perimeter of the foraminous surface;
wherein the margin perimeter is a smooth rectilinear surface;
wherein the margin perimeter is coaxially positioned around the foraminous surface;
wherein the wicking structure is a structure that uses capillary action to draw the therapeutic liquid from the individual applicator;
wherein the wicking structure comprises a frame, an adhesive and a wicking fabric;
wherein the wicking fabric and the adhesive attach to the frame;
wherein the shape of the frame is congruent with the shape of the margin perimeter such that the frame is aligned with and overlaid on the margin perimeter;
wherein the frame attaches to the margin perimeter of the foraminous surface using the adhesive;
wherein the adhesive is a removable and repositionable adhesive;
wherein the wicking fabric is a textile that is formed from hydrophobic filaments;
wherein the frame is formed with a hollow interior such that the wicking fabric is placed in contact with the foraminous surface during use of the medical device;
wherein the medical device further comprises a wall mount;
wherein the wall mount attaches to a wall;
wherein the medical device hangs from the wall mount;
wherein the wall mount comprises a suction cup and a U hook;
wherein the suction cup attaches the U hook to a wall;
wherein the U hook is a hook;
wherein the check valve is a tesla valve;
wherein the handle further comprises a grip;
wherein the grip is an elastomeric material that is applied to the second end of the tube.

* * * * *